United States Patent [19]
Allard et al.

[11] Patent Number: 5,752,963
[45] Date of Patent: May 19, 1998

[54] SUTURE ANCHOR DRIVER

[75] Inventors: Randall N. Allard, Plymouth; Robert D. Krebs, Warsaw; Charles D. Persons, Columbia City; Cary R. Reeves, Leesburg, all of Ind.

[73] Assignee: Bristol-Myers Squibb Company, New York, N.Y.

[21] Appl. No.: 699,286

[22] Filed: Aug. 19, 1996

[51] Int. Cl.$^6$ .................................................. A61B 17/10
[52] U.S. Cl. .......................... 606/139; 606/144; 606/148; 606/232; 606/72
[58] Field of Search ...................... 606/139, 144, 606/148, 232, 72, 73, 75, 60, 142, 143, 76, 77, 78

[56] References Cited

U.S. PATENT DOCUMENTS

| | | | |
|---|---|---|---|
| 5,354,298 | 10/1994 | Lee et al. | 606/72 |
| 5,370,662 | 12/1994 | Stone et al. | 606/232 |
| 5,443,482 | 8/1995 | Stone et al. | 606/232 |

OTHER PUBLICATIONS

Anchorlok™—Questus™ Leading Edge™ Soft Tissue Anchor System—Wright Medical Technology, Inc.–c1995/1996.

Primary Examiner—Michael Powell Buiz
Assistant Examiner—Tina T. D. Pham
Attorney, Agent, or Firm—Cary R. Reeves

[57] ABSTRACT

An improved suture anchor driver includes a handle and an extending elongated shaft adapted for passing through arthroscopic portals. The distal end of the shaft engages the suture anchor. The shaft is cannulated to allow passage of a suture from the anchor to the handle. The shaft also has a slot in its wall and extending along most of its length in communication with the interior of the shaft. The handle has a grooved knob and adjacent resilient cap for retaining a needle. A sliding member is positioned on the shaft adjacent the needle. The intermediate portion of the suture is looped through an elastic hole in order to maintain it in tension. In use, the anchor is driven into tissue. As the driver is withdrawn, the suture pulls out of the elastic hole and through the shaft. The suture then pulls the needle from the groove. A portion of the needle slides in the slot as the needle travels along the cannula. The sliding member is pulled along by the needle. The sliding member protects the needle and helps to control the rate of its withdrawal.

9 Claims, 6 Drawing Sheets

SUTURE ANCHOR DRIVER

BACKGROUND OF THE INVENTION

The present invention relates to an instrument for installing a surgical suture anchor. More particularly, it relates to such an instrument that releasably carries the anchor and a needle and suture connected to the anchor.

During surgery, it is often necessary to attach soft tissue to bone. Many bone anchors have been proposed that carry a suture and attach to bone. The suture is then used with the aid of a needle to secure the soft tissue in close proximity to the bone. It is convenient for the surgeon if the anchor, suture, and needle are preassembled and loaded into a driver for immediate use.

U.S. Pat. No. 5,002,550, issued to Li, teaches a suture anchor installation tool having an end for receiving a suture anchor and a flat rectangular handle for containing a suture and a needle. The handle has chambers for the suture and protruding pins about which the suture is coiled. The handle also contains a curved surface groove in one of its broad flat sides. The radius of curvature of the surface groove is less than the radius of curvature of the needle so that the needle is flexed and rigidly snapped into the groove. A needle cover slidingly engages the handle and can be slid between a position in which it covers the needles and a position in which the needles are exposed. In use, the tool is used to press the suture anchor into a hole in a bone. As the tool is withdrawn, the suture plays out of the tool. The needle is gripped with needle forceps and snapped out of the groove.

U.S. Pat. No. 5,354,298, issued to Lee et al., teaches a suture anchor installation tool having a body and an extending shaft. A suture anchor engages the end of the shaft. The shaft and body have a channel that accommodates a suture passing from the anchor to the body. The suture can be coiled within the body. Needle engaging clips retain needles within the body. A cover may be provided for the body to overlie the suture and needles. After the suture anchor is installed, the needles are removed from the needle retaining clips with a needle gripping instrument.

SUMMARY OF THE INVENTION

The present invention provides an improved suture anchor driver. The driver includes a handle and an extending elongated shaft adapted for passing through arthroscopic portals. The distal end of the shaft engages the suture anchor. The shaft contains a passageway to allow passage of a suture from the anchor to the handle. The shaft also has a slot in its wall and extending along most of its length in communication with the interior of the shaft. The handle has a grooved knob and adjacent resilient cap for retaining a needle. A sliding member is positioned on the shaft adjacent the needle. The intermediate portion of the suture is looped through an elastic hole in the cap in order to maintain it in tension. In use, the anchor is driven into tissue. As the driver is withdrawn, the suture pulls out of the elastic hole and through the shaft. The suture then pulls the needle from the groove. A portion of the needle slides in the slot as the needle travels along the cannula. The sliding member is pulled along by the needle. The sliding member protects the needle and helps to control the rate of its withdrawal.

DETAILED DESCRIPTION OF THE INVENTION

Figure 1:
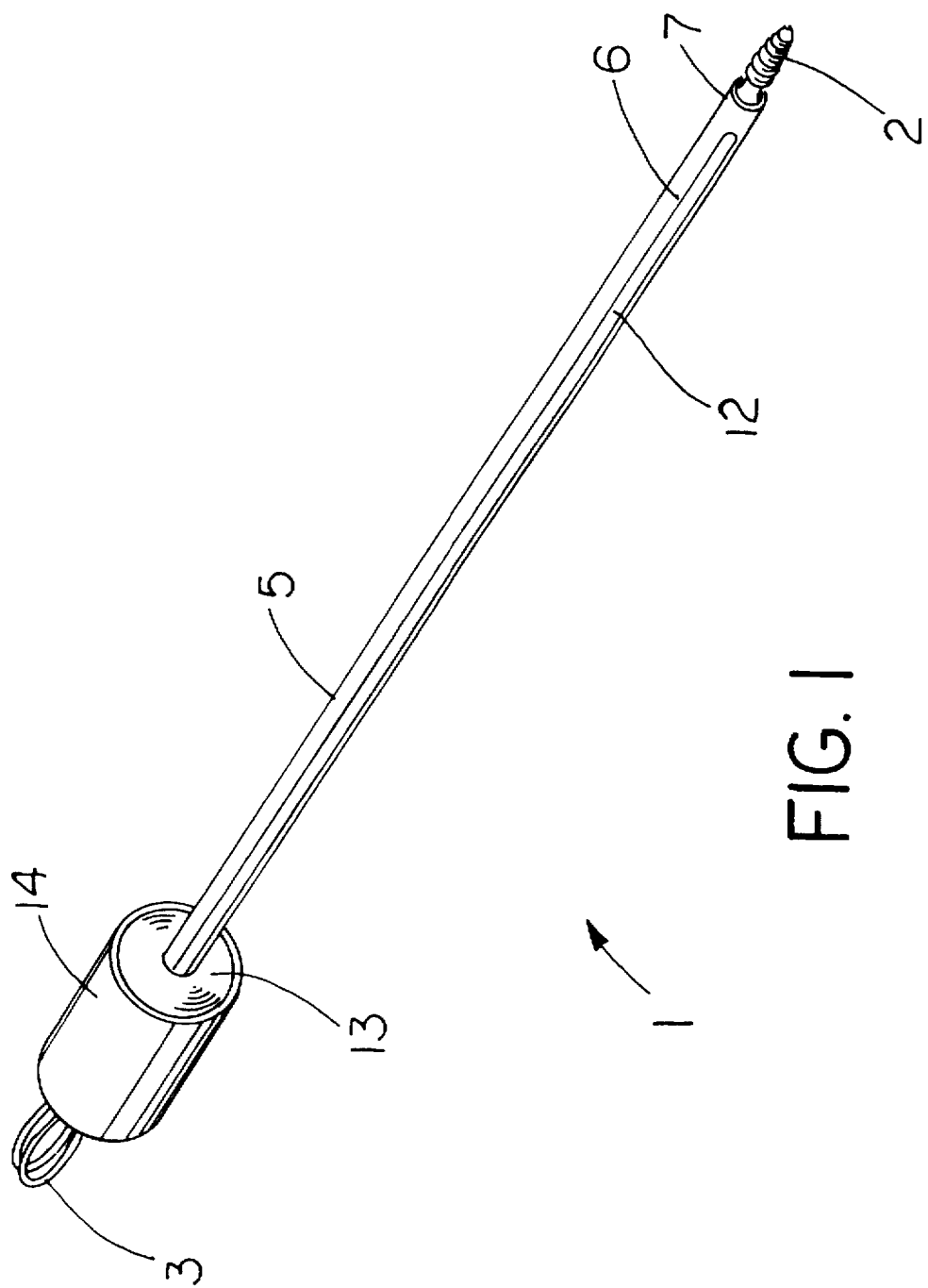
FIG. 1 is a perspective view of the suture anchor driver of the present invention.
Figure 2:
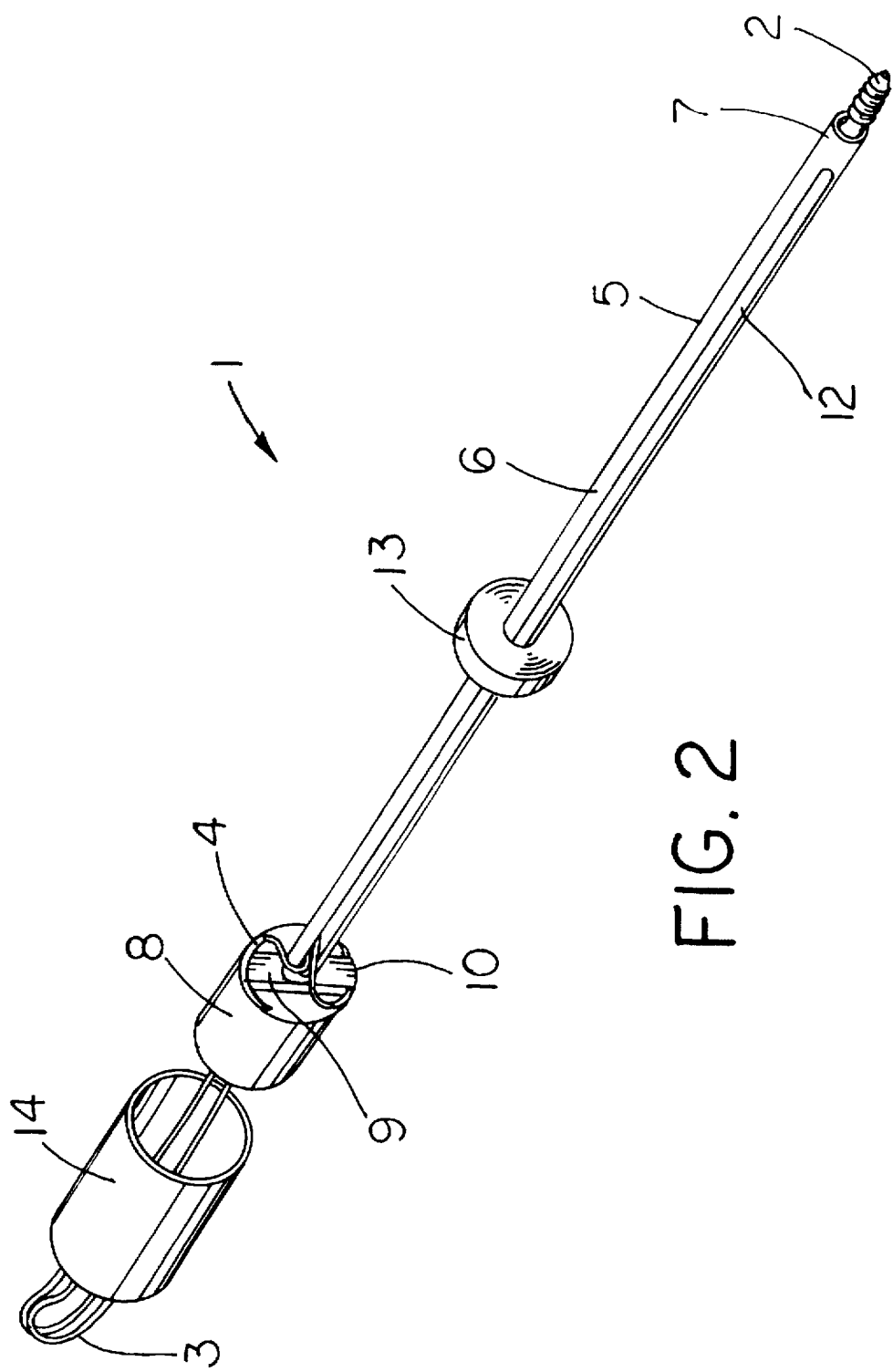
FIG. 2 is a partially exploded view of the suture anchor driver of FIG. 1.
Figure 3:
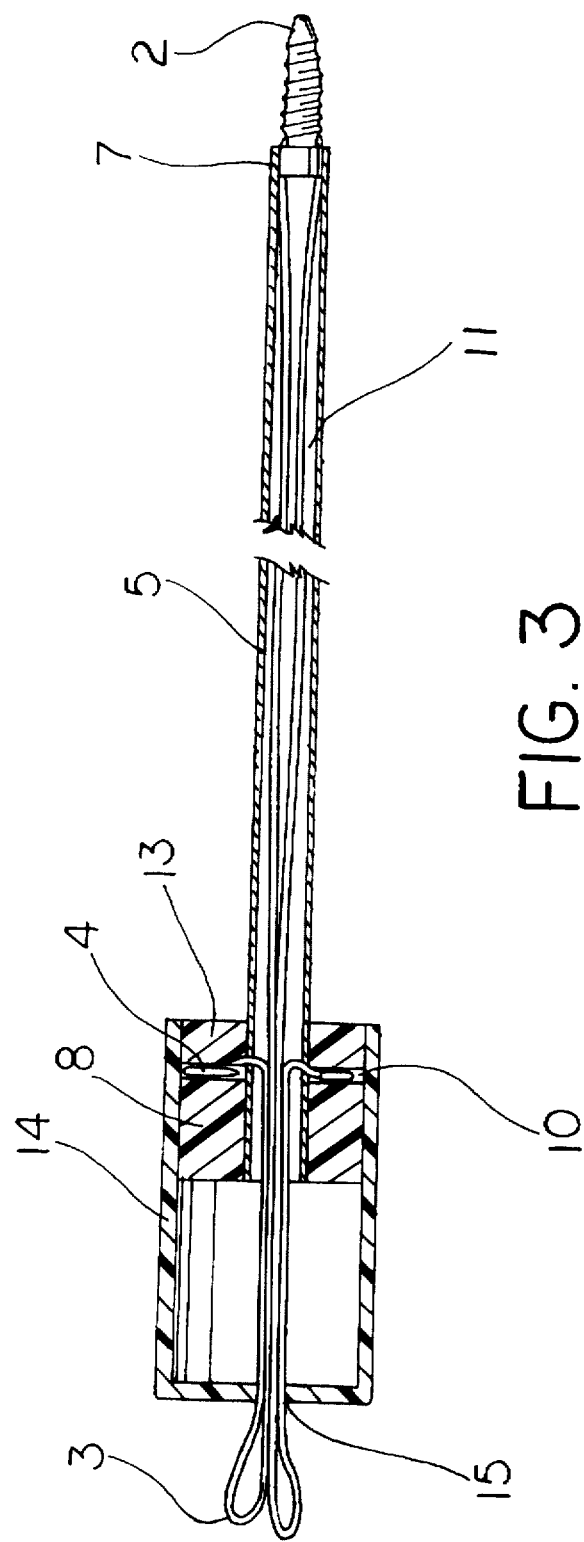
FIG. 3 is a is section view of the suture anchor driver of FIG. 1.

FIGS. 1-3 depict an exemplary suture anchor driver 1 according to the present invention assembled with a suture anchor 2, suture 3, and needle 4. The driver 1 includes an elongated shaft 5 having a longitudinal axis and a sidewall 6. The shaft 5 has an engagement end 7, at its distal portion, for engaging the anchor 2. In the exemplary embodiment shown, the anchor is threaded and requires a rotational force for implantation. Therefore the engagement end 7 and the anchor 2 positively engage one another to allow transmission of rotational force from the driver 1 to the anchor 2. Preferably the shaft 5 is made from a metal tube. The shaft 5 includes a handle at its proximal portion opposite the engagement end 7. The handle includes a knob 8 which helps in gripping the driver 1. The knob 8 can be formed as an integral part of the shaft 5 or, preferably, it can be made as a separate plastic piece that is pressed or bonded to the shaft. A boss 9 extends from the proximal portion of the knob 8. The boss 9 includes a groove 10. In the exemplary embodiment, the boss includes two grooves for two needles. The groove 10 is formed in the side of the boss 9 and lies in a plane transverse to the shaft 5 axis. A passageway 11 inside of the shaft 5 extends from near the engagement end 7 to near the boss 9. In the exemplary embodiment the passageway 11 extends through the boss 9 and knob 8 and exits the back of the knob 8. A slot 12 in the sidewall 6 exposes the passageway 11. A sliding member 13, slidingly engages the shaft 5. The sliding member 13 is preferably made of a resilient plastic material such as polyethylene foam. In the example, the sliding member 13 is in the shape of a toroid in which the inner diameter fits around the shaft 5. Preferably the sliding member 13 is sized to grip the shaft 5 so that it offers some resistance to sliding along the shaft. A cap 14 covers the portion of the knob 8 where the passage 11 exits. Preferably the cap 14 also covers the sides of the knob 8 and extends over the groove 10. A hole 15 is formed in the portion of the cap 14 that overlies the passage 11 exit. Preferably the cap 14 is made of a resilient material such as silicone rubber. The cap 14 can then be stretched to fit tightly over the knob 8. The cap 14 can be slipped or flexed backward on the knob 8 to expose the groove 10. Also, with a resilient material, the hole 15 can be a small pin-hole formed by puncturing the cap without removing any material. Such a pin-hole can be enlarged by stretching and it will snap back to grip an object placed through the hole 15.

Prior to use, the driver 1 is loaded with a suture anchor, suture, and needle as follows: The needle 4 is passed through the passageway 11 from the engagement end to the boss 9. The passageway 11 encloses the suture and keeps it from snagging during use. The needle 4 is passed through the slot 12 and placed in the groove 10. In this position the needle 4 lies in a plane transverse to the axis of the shaft 5. In the case of a curved needle, as shown, the needle 4 curves around the shaft 5. The cap 14 is extended over the groove 10 to hold the needle 4 in the groove 10. The intermediate portion of the suture 3, the portion between the needle 4 and anchor 2, is threaded through the knob 8 and the hole 15. The suture 3 is drawn tight so that the anchor 2 engages the engagement end 7. The sides of the hole 15 grip the suture 3 and hold it in tension. The sliding member 13, is slid up the shaft 5 until it rests against the boss 9. The cap 14 can be extended to overlie and grip the sliding member 13 to hold it in this position. Alternatively, the boss 9 and groove 10 can be eliminated and the sliding member 13 positioned to hold the needle 4 against the bottom of the knob 8. Once loaded, the driver 1 holds the suture anchor, suture, and needle in tension in a state of readiness.

Figure 4:
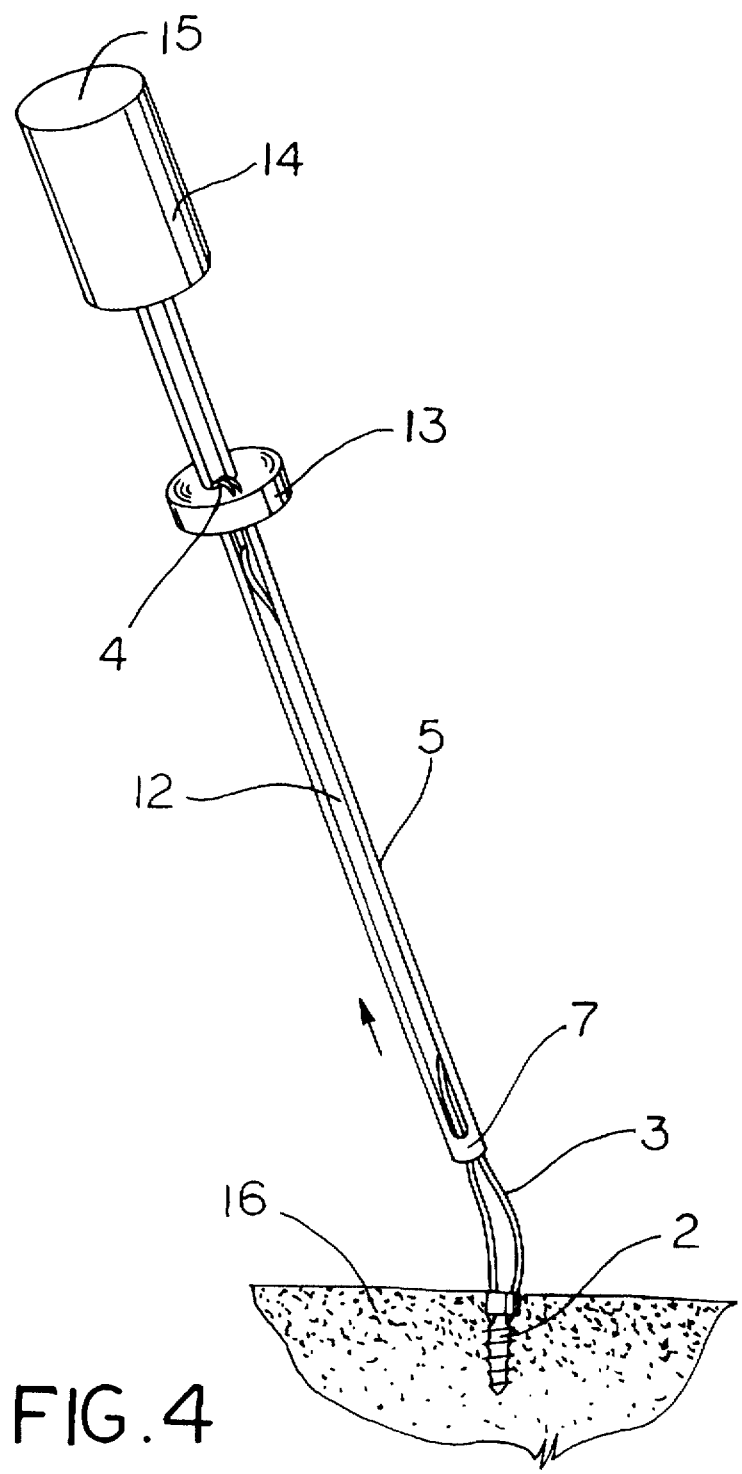
FIG. 4 is a perspective view showing the suture anchor driver of FIG. 1 in use.
Figure 5:
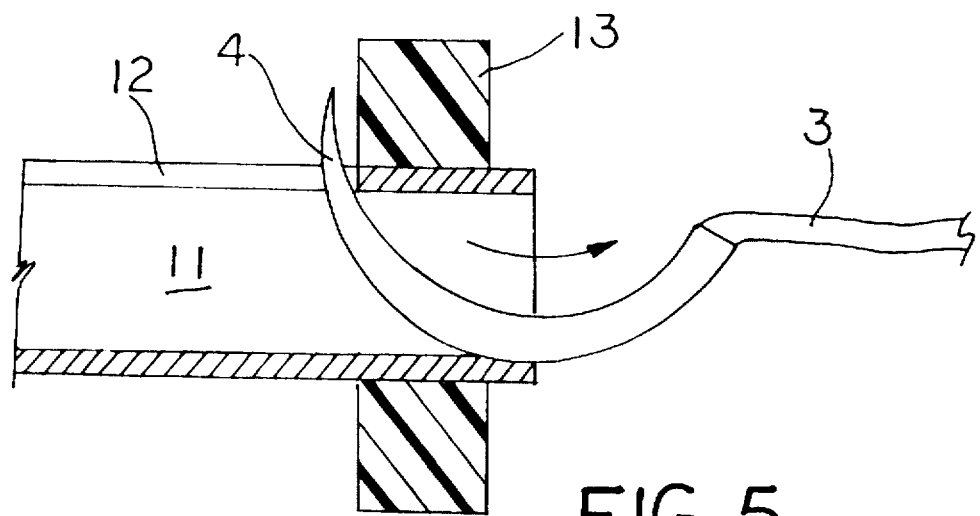
FIG. 5 is a section view of the distal end of the suture anchor driver of FIG. 1 showing a needle just before it exits the driver.

In use, as shown in FIG. 4, the anchor 2 is driven into tissue 16 and the driver is withdrawn. As the driver 1 is withdrawn, the suture 3 plays out of the driver 1 along the passageway 11. First, the intermediate portion pulls through the hole 15 and passageway 11. When the suture 3 pulls on the needle 4, the needle 4 presses against the side of the cap 14 which flexes out of the way to release the needle 4 from the groove 10. The needle 4 enters the passageway 11 by way of the slot 12. As the needle 4 moves down the passageway 11, a portion of it may extend out of the passageway 11 through the slot 12. This allows the shaft 5 diameter to be smaller than the arch height of a curved needle 4. As the needle 4 moves along the passageway 11, the portion extending through the slot 12 bears against the sliding member 13 and pulls it along the shaft 5. The sliding member 13 slows the progress of the needle 4, or in other words, controls the needle's rate of withdrawal by checking its velocity. In addition, the sliding member 13 protects the needle's point, maintains the needle 4 inside the passageway 11 and slot 12, and maintains tension in the suture 3 to improve the user's control of the deployment. In the exemplary embodiment, the slot 12 stops short of the distal end of the shaft 5. The slot is placed near enough to the distal end that the needle 4 can enter the passageway 11 and curve into the slot 12 as shown in FIG. 5. On deployment, the needle contacts the side wall 6 adjacent the end of the slot 12. The needle 4 then rotates out of contact with the sliding member 13 and side wall 6 and exits the driver 1.

In the preferred embodiment shown in FIGS. 1–5, two suture ends extend from the suture anchor 2 and a needle 4 is attached to each end. The needles 4 can be positioned in grooves 10 on opposite sides of the knob 8, as shown, or they can both be placed in the same groove 10. It has been found that deployment of the needles 4 is smoother if they are placed in the same groove 10.

Figure 6:
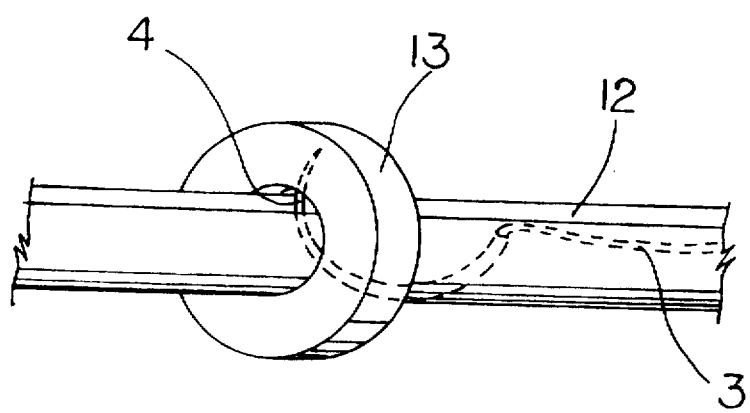
FIG. 6 is a perspective view of the sliding member of the suture anchor driver of FIG. 1 showing an alternative loading arrangement.

FIG. 6 illustrates an alternative way that the needle 4 can be loaded in the driver 1. The needle 4 extends through the slot 12 and is embedded in the sliding member 13. The sliding member is then positioned adjacent the knob 8. When the anchor 2 is deployed, the suture 3 pulls the needle 4 which pulls the sliding member 13 along the shaft 5. When the needle 4 approaches the distal end of the shaft 5, it contacts the side wall 6 adjacent the end of the slot 12 and rotates out of the sliding member 13 and exits the driver 1.

Figure 8:
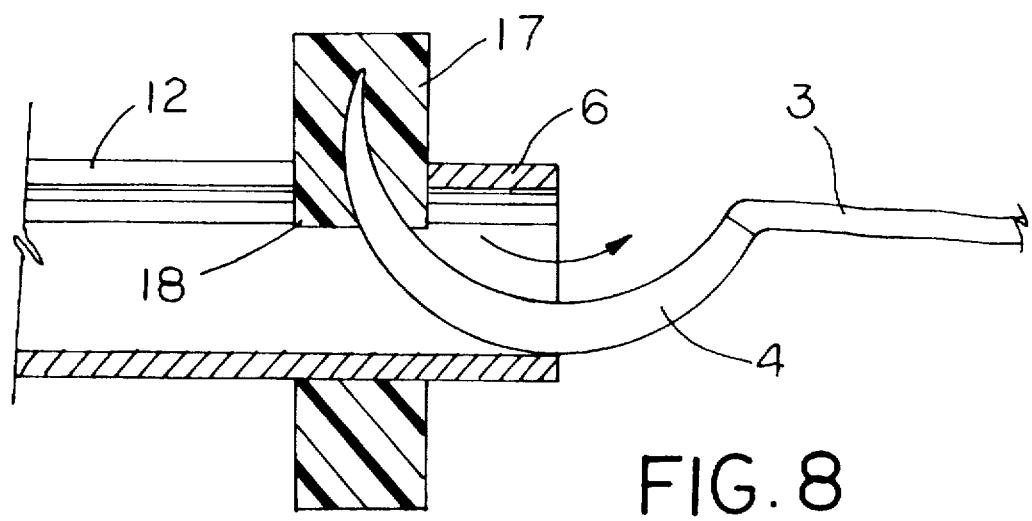
FIG. 8 is a section view of the distal end of a suture anchor according to the resent invention using the sliding member of FIG. 7 loaded according to FIG. 6 showing a needle just before it exits the driver.
Figure 7:
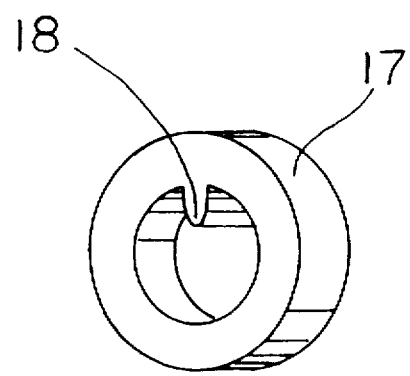
FIG. 7 is a perspective view of an alternative embodiment of a sliding member.

FIG. 7 illustrates an alternative sliding member 17. A tab 18 extends inwardly from the inner diameter of the sliding member 17. The tab 18 engages the slot 12. When the sliding member 17 approaches the distal end of the shaft 5, the tab 18 contacts the side wall 6 adjacent the end of the slot 12 thus halting the progress of the sliding member 17. The needle 4 then rotates out of contact with the sliding member, or out of the sliding member in the alternative loading arrangement shown in FIG. 6, and exits the driver 1. FIG. 8 shows the needle 4 just before it exits the driver 1, when using the sliding member of FIG. 7 loaded according to FIG. 6.

Figure 9:
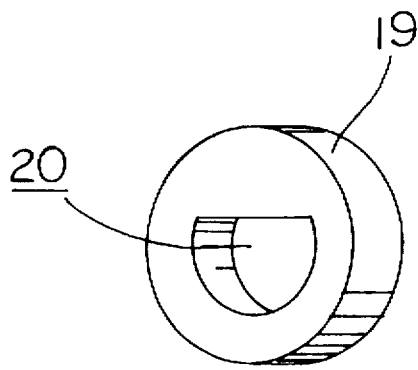
FIG. 9 is a perspective view of another alternative embodiment of a sliding member.

FIG. 9 illustrates an alternative sliding member 19 having a non-circular hole 20 for engaging the shaft 5. A D-shaped hole is shown. When the sliding member 19 is placed on the shaft 5, a portion of the resilient material is forced into the slot 12 thus forming a tab as described above.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A suture anchor driver for driving a suture anchor of the type having an anchor, a suture connected to the anchor, and a needle connected to the suture, the suture anchor driver comprising:

a shaft having a longitudinal axis and a sidewall, the shaft having an engagement end for engaging a said anchor;

needle holding means positioned adjacent the shaft for releasably holding a said needle;

path means communicating between the needle holding means and the engagement end, the path means being able to contain a said suture extending between a said anchor in engagement with the engagement end and a said needle being held by the needle holding means, the path means also being able to accommodate passage of a said needle along the path's length when a said suture is pulled from the driver, the withdrawal of the shaft away from a said anchor once a said anchor is implanted causing a said suture to play out along the path means and release a said needle from the needle holding means and pull a said needle along the path means; and a cap mounted on the shaft opposite the engagement end, the cap having a hole for receiving a portion of a said suture, the cap being made of a resilient material so that it can be stretched under force to enlarge the hole and so that it will snap back to shrink the hole when the stretching force is reduced.

2. The suture anchor driver of claim 1 wherein the needle holding means comprises a groove in which a said needle lies, the cap extending over the groove to hold a said needle in the groove.

3. The suture anchor driver of claim 2 wherein the path means includes a hollow passageway along the shaft axis and a slot in the shaft wall, the slot exposing the passageway along a portion of its length, the path means being able to pass a said needle with a portion of a said needle extending into the slot.

4. The suture anchor driver of claim 3 wherein the slot stops before reaching the engagement end, the passageway extending to the engagement end.

5. The suture anchor driver of claim 3 wherein a portion of the sliding member extends into the slot, the portion abutting the end of the slot when the sliding member is positioned at the end of the slot.

6. The combination of a suture anchor and suture anchor driver, the combination comprising:

a suture anchor;

a suture connected to the anchor;

a needle connected to the suture;

a shaft having a longitudinal axis and a sidewall, the shaft having an engagement end in engagement with the anchor;

a needle holder positioned adjacent the shaft releasably holding the needle;

a passageway in the shaft communicating between the needle holder and the engagement end; and a sliding member, the sliding member being mounted in sliding engagement with the shaft, the sliding member being slidable between a first position near the needle holder and a second position near the engagement end, the sliding member gripping the shaft so that it offers some resistance to sliding from the first position to the second position, the sliding member being engageable with the needle so that the sliding member's resistance to sliding slows the progress of the needle as it is withdrawn from the driver.

7. The combination of claim 6 further comprising a cap mounted on the shaft opposite the engagement end, the cap having a hole, a portion of suture being looped through the hole, the cap being made of a resilient material so that it can be stretched under force to enlarge the hole and so that it will snap back to shrink the hole and grip the portion of the suture when the stretching force is reduced.

8. The combination of claim 7 wherein the needle holder comprises a knob mounted on the shaft, the knob containing a groove in which the needle lies, the cap extending over the groove to hold the needle in the groove, the cap flexing to release the needle from the groove in response to a pull on the suture directed along the passageway.

9. The combination of claim 8 further including a slot in the shaft wall, the slot exposing the passageway along a portion of its length, the slot being sized to receive a portion of the needle when the needle is pulled along the passageway.

* * * * *